(12) United States Patent
Rembert et al.

(10) Patent No.: US 8,621,244 B1
(45) Date of Patent: Dec. 31, 2013

(54) METHOD AND APPARATUS FOR MATCHING CONSUMERS

(71) Applicant: Datalogix Inc., Westminster, CO (US)

(72) Inventors: Jason James Rembert, Longmont, CO (US); Isabella Maria Castrillo, Westminster, CO (US)

(73) Assignee: Datalogix Inc., Westminster, CO (US)

( * ) Notice: Subject to any disclaimer, the term of this patent is extended or adjusted under 35 U.S.C. 154(b) by 0 days.

(21) Appl. No.: 13/644,736

(22) Filed: Oct. 4, 2012

(51) Int. Cl.
*G06F 21/00* (2013.01)

(52) U.S. Cl.
USPC .......................................... 713/193; 707/752

(58) Field of Classification Search
None
See application file for complete search history.

(56) References Cited

U.S. PATENT DOCUMENTS

| | | | |
|---|---|---|---|
| 5,111,395 A | 5/1992 | Smith et al. | |
| 5,499,359 A | 3/1996 | Vijaykumar | |
| 5,819,291 A * | 10/1998 | Haimowitz et al. | 1/1 |
| 6,026,398 A | 2/2000 | Brown et al. | |
| 6,061,798 A * | 5/2000 | Coley et al. | 726/12 |
| 6,523,041 B1 | 2/2003 | Morgan et al. | |
| 6,697,799 B1 | 2/2004 | Neal et al. | |
| 7,257,596 B1 | 8/2007 | Williams et al. | |
| 7,461,263 B2 | 12/2008 | Prince | |
| 7,577,680 B1 | 8/2009 | Williams et al. | |
| 7,904,337 B2 | 3/2011 | Morsa | |
| 7,912,865 B2 | 3/2011 | Akerman et al. | |
| 7,992,210 B2 | 8/2011 | McKenna | |
| 8,135,747 B2 | 3/2012 | Anzalone et al. | |
| 8,136,034 B2 | 3/2012 | Stanton et al. | |
| 8,185,437 B2 | 5/2012 | Altberg et al. | |
| 2002/0082901 A1 | 6/2002 | Dunning et al. | |
| 2005/0071239 A1 | 3/2005 | Tormey et al. | |
| 2009/0182702 A1 | 7/2009 | Miller | |
| 2009/0198653 A1 | 8/2009 | Christianson | |
| 2009/0216641 A1 | 8/2009 | Hubbard | |
| 2009/0313463 A1 * | 12/2009 | Pang et al. | 713/150 |
| 2010/0094758 A1 | 4/2010 | Chamberlain et al. | |
| 2010/0223104 A1 | 9/2010 | Patel et al. | |
| 2010/0325142 A1 | 12/2010 | Anzalone et al. | |
| 2011/0016042 A1 | 1/2011 | Cho et al. | |
| 2012/0054189 A1 | 3/2012 | Moonka et al. | |
| 2012/0059714 A1 | 3/2012 | Furman et al. | |
| 2012/0078922 A1 | 3/2012 | Skurtovich, Jr. et al. | |
| 2012/0158574 A1 | 6/2012 | Brunzell et al. | |
| 2012/0173374 A1 | 7/2012 | Soroca et al. | |

\* cited by examiner

*Primary Examiner* — Gilberto Barron, Jr.
*Assistant Examiner* — Izunna Okeke
(74) *Attorney, Agent, or Firm* — Cooley LLP (57) ABSTRACT

In some embodiments, a method includes receiving a first record set from a first compute device and a second record set from a second compute device. Each record from the first record set has a first attribute string; and each record from the second record set has a first attribute string. The method includes defining a third record set to include each record from the first record set that has a first attribute string equal to a first attribute string of a record from the second record set. The method also includes repeating the above steps for a fourth record set from the first compute device and a fifth record set from the second compute device to further define the third record set. Each record from the fourth record set has a second attribute string and each record from the fifth record set has a second attribute string.

16 Claims, 6 Drawing Sheets

| | A | B |
|---|---|---|
| 7 | sally.doe@test.com | 444444444 |
| 8 | jane.doe@test.com | 222222222 |
| 9 | john.doe@test.com | 555555555 |
| 10 | mary.doe@test.com | 333333333 |
| 11 | harry.doe@test.com | 111111111 |

FIG. 4A

| | A | B |
|---|---|---|
| 7 | sally.doe@test.com | 666666666 |
| 8 | jane.doe@test.com | 777777777 |
| 9 | john.doe@test.com | 888888888 |
| 10 | mary.doe@test.com | 999999999 |
| 11 | harry.doe@test.com | 101010101 |

FIG. 4B

| | A | B |
|---|---|---|
| 1 | e170c5e297a6e342fa7c6b24fb4c7e9c101␌e983 | 8X0bI5+TTayN4FxUDOeiPqW6XuL1R5B4X8YIakVKu2I= |
| 2 | 780b026245305e4a93fc2d189a4bcd03a405b924 | qFkW1A1ThCGQsTa8VWYBSlnSTPB6yYWuNO0upR9GI4= |
| 3 | c7b57c1e30c710de01c353b161df24c2c7b593a8 | RQbe7d1bPVe4aQF0J4vLZ5QjhIMIJjemO1WjY4eGAVs= |
| 4 | 98426a4f6ab1b26773fe7d2353Sebe7da46df806 | bl84pcfVWOOeJEB/7XVwpaAON2viW2toS8uefG0cICg= |
| 5 | 0e856b5710b6da18eb864d1c9a4a7042832ac725 | 3W/g+/nyBnhrRyMz1ydHdZ+3Ui8aVWF89yapOCGq38= |

FIG. 4C

| | A | B |
|---|---|---|
| 1 | e170c5e297a6e342fa7c6b24fb4c7e9c101␌e983 | OOJx0YMR68okJcjgs6kRPC9ahqDYmpRSbPEq8da7aTw= |
| 2 | 780b026245305e4a93fc2d189a4bcd03a405b924 | 2Ry4hkpL66QEEcxcZShwE8qLkjwrr9RwbpOWJE2e25I= |
| 3 | c7b57c1e30c710de01c353b161df24c2c7b593a9 | FEJJ+IK5zwvbG2RQYjsDnqdefz/DgI7Qp2W0scfsWYg= |
| 4 | 98426a4f6ab1b26773fe7d2353Sebe7da46df806 | 2JZ+VgjcBkQ5oV8BnHmcrxJ37eM6lue6GgduxA96o= |
| 5 | 0e856b5710b6da18eb864d1c9a4a7042832ac725 | PAcqjA1Dovt8ugBc3i5hyq96gReiS5L/GwWDyU/OOM= |

FIG. 4D

| A | B |
|---|---|
| 7 | doe,john,denver,co | 555555555 |
| 8 | doe,mary,westminster,co | 333333333 |
| 9 | doe,harry,arvada,co | 111111111 |
| 10 | doe,jane,golden,co | 222222222 |
| 11 | doe,sally,boulder,co | 444444444 |

FIG. 4E

| A | B |
|---|---|
| 7 | doe,john,denver,co | 666666666 |
| 8 | doe,mary,westminster,co | 777777777 |
| 9 | doe,harry,arvada,co | 888888888 |
| 10 | doe,jane,golden,co | 999999999 |
| 11 | doe,sally,boulder,co | 101010101 |

FIG. 4F

| A | B |
|---|---|
| 1 | c5c6132f6bf2e9f37c9dba42ea059dd1e891af837 | RQbe7d1bPve4aQfDI4vL25QjhMUjemOIWjY4eGAVs= |
| 2 | b07kc9191116c5fcb1031b66930ff05779a757190 | bI84pcfVWOOejEB/7xVwpaADN2wWzto58uefG0cfCg= |
| 3 | 7a16bb75a05715a3970f692e56b926c22ff04c434 | 3Wig+/my8nhrRyMz1ydHdZ+3Ui8aVWF89yaap0CGq38= |
| 4 | 7f1c3f7b9ee5f940ded2e46e4011a90f3afb196 | qfkWIA1ThcGQqTa8vWyBSn5TP8gryWuNO0upR9GI+4= |
| 5 | bb40702eebac0fdc23b771cc3b0e436a99b3ddd8 | 8X0b15+TTayN4FxUOeIPqW6XUL1R5B4X8Y1akVKU2I= |

FIG. 4G

| A | B |
|---|---|
| 1 | c5c6132f6bf2e9f37c9dba42ea059dd1e891af837 | OOJxi0YMR68oKicigs6kPQ9ahqOYmpRSbPEq8da7aTw= |
| 2 | b07kc9191116c5fcb1031b66930ff05779a757190 | ZRlyskh6pL66OEFcXcZShwF8oLXJwn9RWbpOWlEZeZ5l= |
| 3 | 7a16bb75a05715a3970f692e56b926c22ff04c434 | FEJj+K5zwwbGZRQrjs0nGd6fz/0gi7QP2WDscfsWYg= |
| 4 | 7f1c3f7b9ee5f940ded2e46e4011a90f3afb196 | 2i2+vcJvss0ruVv8nhmcrxJJ7eM6Iue6GgGduxAI96o= |
| 5 | bb40702eebac0fdc23b771cc3b0e436a99b3ddd9 | PAcqIAIDovt8ug8c3I5Hvq9q6Rel5SL/GwWDyU/QOM= |

```
waterfall.lst
1  email.csv
2  lastname,firstname,city,state.csv
```

FIG. 4J

| | A | B |
|---|---|---|
| 13 | 99999999 | 33333333 |
| 14 | 66666666 | 44444444 |
| 15 | 10101010 | 11111111 |
| 16 | 77777777 | 22222222 |

FIG. 4K

| | A | B |
|---|---|---|
| 13 | 99999999 | 22222222 |
| 14 | 88888888 | 11111111 |
| 15 | 66666666 | 55555555 |
| 16 | 77777777 | 33333333 |

FIG. 4L

| | A | B |
|---|---|---|
| 13 | 99999999 | 33333333 |
| 14 | 88888888 | 11111111 |
| 15 | 66666666 | 44444444 |
| 16 | 10101010 | 11111111 |
| 17 | 77777777 | 22222222 |

METHOD AND APPARATUS FOR MATCHING CONSUMERS

BACKGROUND

Some embodiments described herein relate generally to methods and apparatus for matching consumers.

Marketing collaborators, for example marketing entities, websites, online and offline stores, and data analytics entities can share information in order to plan, execute, and measure marketing and other efforts. Systems and methods for information sharing, particularly customer information sharing and matching exist, but can often run afoul of privacy polices and/or laws. Furthermore, such systems may not effectively match information from one entity with information from other entities because they can use limited information which can result in missing a match where one exists.

A need exists, therefore, for improved methods and apparatus for matching consumers.

SUMMARY

In some embodiments, a method includes receiving, from a first compute device, a first record set. Each record from the first record set includes an encrypted first identification string and a hashed first attribute string. The method includes receiving, from a second compute device, a second record set. Each record from the second record set has an encrypted second identification string and a hashed first attribute string. The method further includes defining a third record set to include each record from the first record set that has a hashed first attribute string equal to a hashed first attribute string of a record from the second record set. Each record from the third record set includes an encrypted first identification string and an encrypted second identification string. The method also includes repeating the above steps for a fourth record set from the first compute device and a fifth record set from the second compute device to further define the third record set. Each record from the fourth record set has an encrypted first identification string and a hashed second attribute string and each record from the fifth record set has an encrypted second identification string and a hashed second attribute string.

DETAILED DESCRIPTION

In some embodiments, a method includes receiving a first record set from a first compute device. Each record from the first record set includes an encrypted first identification string and a hashed first attribute string. The method includes receiving a second record set from a second compute device. Each record from the second record set includes an encrypted second identification string and a hashed first attribute string. In some embodiments, the hashed first attribute string can be based on, for example, an email address, a zip code, a portion of a name, and/or the like. Based on the first record set and the second record set, a third record set is defined to include each record from the first record set that has a hashed first attribute string equal to a hashed first attribute string of a record from the second record set. Each record from the third record set includes an encrypted first identification string and an encrypted second identification string.

Similarly, the method includes receiving a fourth record set from the first compute device. Each record from the fourth record set includes an encrypted first identification string and a hashed second attribute string. The method includes receiving a fifth record set from the second compute device. Each record from the fifth record set includes an encrypted second identification string and a hashed second attribute string. The method further includes defining a sixth record set to include each record from the fourth record set that has a hashed second attribute string equal to a hashed second attribute string of a record from the fifth record set. Each record from the sixth record set includes an encrypted first identification string and an encrypted second identification string.

In some embodiments, the method can further include modifying the sixth record set to a modified state to exclude each record from the sixth record set that has an encrypted first identification string equal to an encrypted first identification string of a record from the third record set. A matched record set can be defined to include each record from the third record set and each record from the sixth record set in the modified state. Furthermore, a signal indicative of the matched record set can be sent to the first compute device and/or the second compute device.

As used herein, a module can be, for example, any assembly and/or set of operatively-coupled electrical components, and can include, for example, a memory, a processor, electrical traces, optical connectors, software (executing in hardware), and/or the like. As used herein, the singular forms "a," "an" and "the" include plural referents unless the context clearly dictates otherwise. Thus, for example, the term "a record database" is intended to mean a single database or a set of databases with similar functionalities. Furthermore, as described herein, an entity, for example a business entity associated with a compute device, can be a marketing entity, a website and/or website operator, an online and/or an offline store, a data analytics entity, etc.

Figure 1:
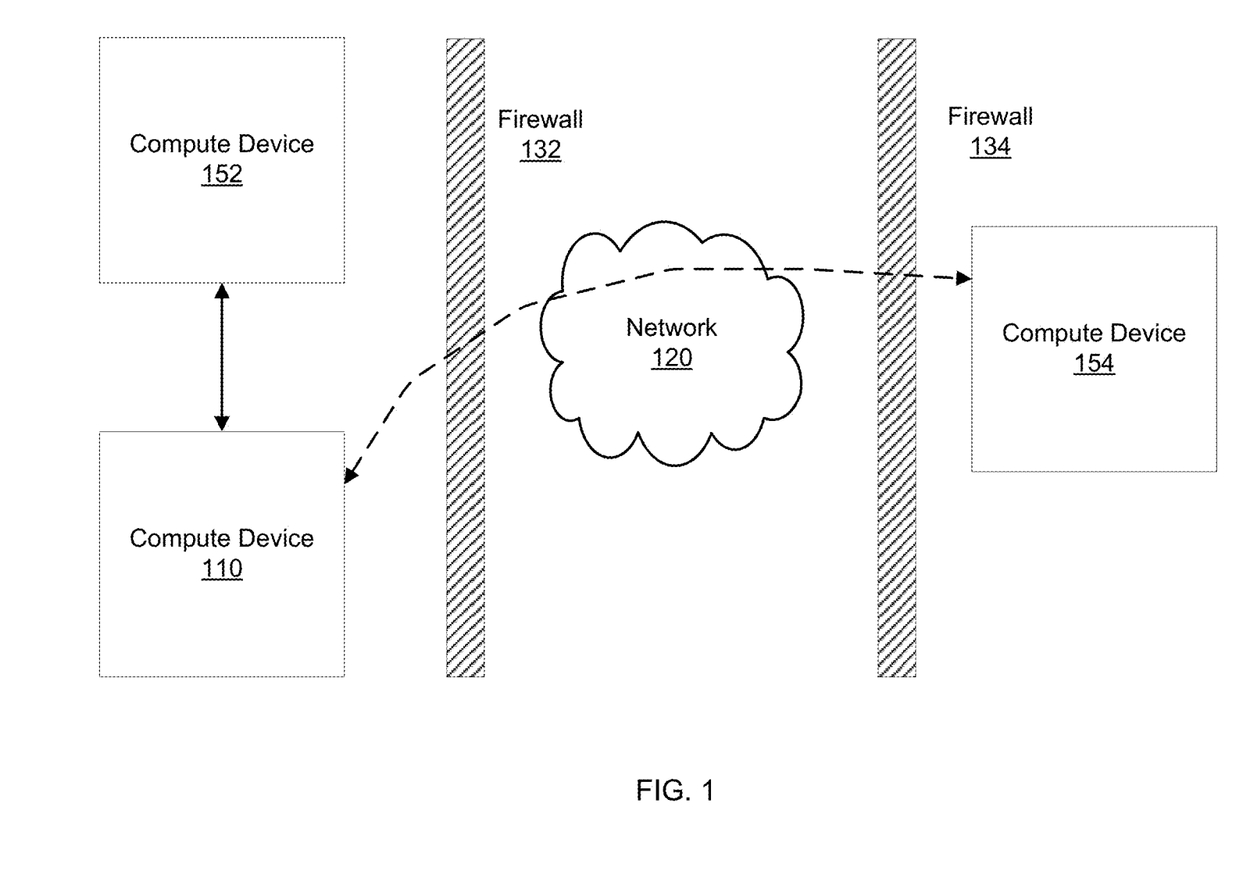
FIG. 1 is a schematic illustration of multiple compute devices configured to match record sets, according to an embodiment.

FIG. 1 is a schematic illustration of multiple compute devices 110, 152 and 154 configured to match record sets, according to an embodiment. As shown in FIG. 1, the compute device 110 is directly or operatively coupled to the compute device 152. The compute device 110 is also operatively coupled to the compute device 154 via at least a first firewall 132, a network 120 and a second firewall 134. As described below, the compute devices 110, 152 and 154 can be configured to, in coordination, perform a process to match records from multiple record sets.

The firewall 132 or 134 can be any software-based module and/or hardware-based device that is used to control and filter incoming and/or outgoing network traffic. The firewall 132 or 134 can be used to separate an internal network and an external network, thus to keep the internal network secure from the external network. In the example shown in FIG. 1, the firewall 132 separates an internal network that includes the compute device 152 and the compute device 110 from the external network 120; and the firewall 134 separates an internal network that includes the compute device 154 from the external network 120. In some embodiments, the firewall 132 or 134 can be, for example, a network-layer firewall (e.g., a packet filter firewall), a circuit-level firewall, an application-layer firewall, a proxy server, etc.

The network 120 can be any type of network that is external to the internal network behind the firewall 132 and the internal network behind the firewall 134, and connects the two internal networks (through the firewalls 132 and 134). The network 120 can be a wired network, a wireless network, or a combination wired/wireless network. In some embodiments, the network 120 can be, for example, a local area network (LAN), a wide area network (WAN), a wireless LAN (WLAN), the Internet, and/or the like.

A compute device (e.g., the compute device 110, 152, or 154) can be any device configured to produce, store, manipulate, and/or perform any other operation on one or more record sets. Such a compute device can be, for example, a server, a workstation, a data center, a data processing computer, or any other type of computing device or combination of computing devices.

In some embodiments, different compute devices can be configured to perform different functions. In the example of FIG. 1, the compute devices 152 and 154 can be configured to generate data files containing original record sets that are to be matched with other original record sets. Specifically, the compute device 152 and 154 can be configured to, for example, access and retrieve data from an external resource (e.g., a storage device), define one or more record sets based on the retrieved data, concatenate the defined record sets appropriately to generate one or more data files, store the data file(s) in a memory, send the data file(s) including the record sets to other devices (e.g., the compute device 110), and/or the like. On the other hand, the compute device 110 can be configured to match records from multiple original record sets to define one or more matched record sets. Specifically, the compute device 110 can be configured to, for example, receive data files containing original record sets (e.g., from the compute devices 152 and 154), compare and match records from multiple original record sets to define a matched record set, store the matched record set in a memory, send the matched record set to other devices (e.g., the compute device 152 or 154), and/or the like.

A record set defined and/or processed at the compute device 152, 154 or 110 can be any type of data structure that stores data in a data file. An original record set can be defined at the compute device 152 or the compute device 154, and further processed (e.g., compared to other original record set(s) to define a matched record set) at the compute device 110. A record set (e.g., an original record set, a matched record set) can be, for example, an array, a list, a table, a queue, a tree, a map, a graph, or any other suitable type of data structure. Data stored in a record set can be associated with, for example, users of a service, clients of a company, registered viewers of an online forum, buyers of a product, and/or the like. Such data can include, for example, an email address of a buyer, a login identification of an online viewer, a name (e.g., a surname, a first name) of a user, an address (e.g., a zip code, a street address) of a company, and/or the like.

In some embodiments, the compute devices 152 and 110 can be associated with a first entity such as, for example, a company, an organization, an individual, etc. In such embodiments, the compute devices 152 and 110 can be included in a first internal network (not shown in FIG. 1) that is associated with the first entity and separated from the external network 120 (e.g., the Internet) by the firewall 132. The compute device 152 and the compute device 110 can be directly coupled to each other or co-located on a single device (e.g., a data center) within the first internal network. Alternatively, the compute device 152 and the compute device 110 can be separate devices that are operatively coupled to each other via one or more other devices such as, for example, a service device, a routing device, another compute device, and/or the like. In some embodiments, the compute device 152 and the compute device 110 can be one compute device. In such embodiments, such a compute device can define original records sets and also define matched record sets based on multiple original records sets defined at that compute device and/or received from other compute device (e.g., the compute device 154). In addition, the record set(s) defined at the compute device 152 can be based on data associated with the first entity. For example, the first entity can be an online company, and the record sets defined at the compute device 152 can include data associated with registered users of a website of the company.

Similarly, the compute device 154 can be associated with a second entity (e.g., a company, an organization, an individual, etc.) different from the first entity. Thus, the compute device 154 can be included in a second internal network (not shown in FIG. 1) that is associated with the second entity and separated from the external network 120 (e.g., the Internet) by the firewall 134. In such embodiments, as shown in FIG. 1, the compute device 154 can be operatively coupled to the compute device 110 via at least the firewall 134, the network 120 and the firewall 134. In addition, the record set(s) defined at the compute device 154 can be based on data associated with the second entity. For example, the second entity can be a data analytics entity, and the record sets defined at the compute device 154 can include data associated with shoppers of one or more retail chain stores.

In some embodiments, although not shown in FIG. 1, the first internal network and/or the second internal network can be separated from the external network 120 by more than one firewall, or no firewall. In such embodiments, the compute device 110 and the compute device 154 can be coupled (directly or operatively) to each other via any number of firewalls, or without being separated by any firewall. Furthermore, in some embodiments, the compute device 110 can be external to both the first internal network and the second internal network. For example, the compute device 110 can be associated with a third entity different from the first entity and the second entity. As a result, the compute device 110 can be included in the network 120 between the firewall 132 and the firewall 134. In such embodiments, the compute device 110 can be operatively coupled to the compute device 154 via the firewall 132, and operatively coupled to the compute device 152 via the firewall 134.

In some embodiments, although not shown in FIG. 1, the compute device 110 can be operatively coupled to a fourth compute device via the firewall 132, the network 120, and/or a third firewall. The fourth compute device can be associated with a third entity different from the first entity and the second entity. Thus, the compute device 110 can receive record sets from the compute device 152, the compute device 154 and the fourth compute device, and perform a process to match records from the received records sets in a similar way as described herein with respect to FIG. 3.

Figure 2:
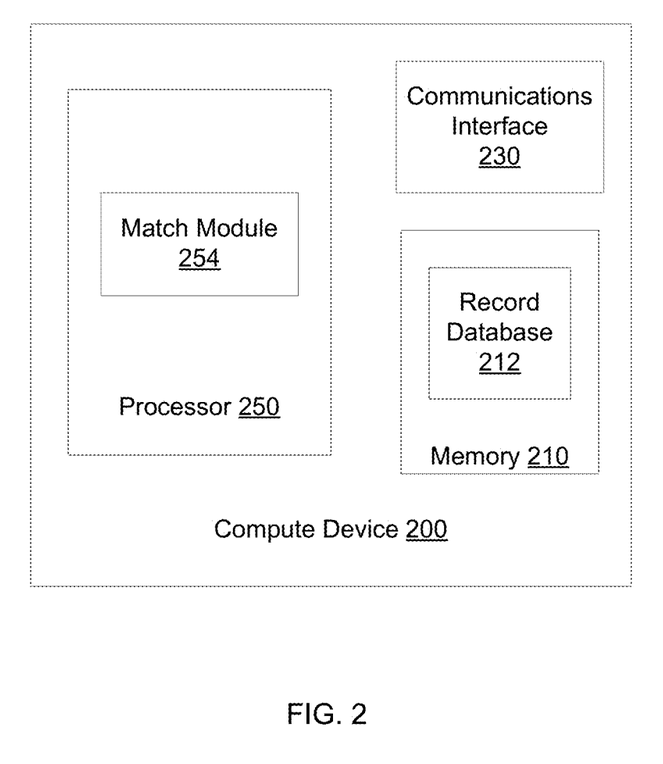
FIG. 2 is a block diagram of a compute device, according to an embodiment.

FIG. 2 is a block diagram of a compute device 200, according to an embodiment. The compute device 200 can be a compute device configured to match record sets received from other compute devices, similar to the compute device 110 in FIG. 1. As shown in FIG. 2, the compute device 200 includes a communications interface 230; a memory 210, which contains a record database 212 (e.g., storage for one or more data files, a relational database, etc); and a processor 250, which contains a match module 254. Operations of the communications interface 230 (e.g., transmit/receive data files) and the match module 254 (e.g., comparing record sets, producing a matched record set), as well as manipulations on the record database 212 (e.g., storing a data file, deleting a data file) or any other portion of the memory 210, can be controlled by the processor 250.

In some embodiments, the communications interface 230 of the compute device 200 can be associated with one or multiple ports (for wired connections, not shown in FIG. 2) and/or antennas (for wireless connections, not shown in FIG. 2) of the compute device 200. The communications interface 230 and the associated ports and/or antennas can be used to implement one or more wired and/or wireless connections between the compute device 200 and other compute devices (e.g., the compute devices 152, 154 in FIG. 1) or other devices (e.g., a display device, a storage device). Among those connections, the wired connections can be, for example, twisted-pair electrical signaling via electrical cables, fiber-optic signaling via fiber-optic cables, and/or the like; and the wireless connections can be based on any suitable wireless communication protocols (e.g., a Bluetooth protocol, a Wi-Fi protocol, etc.). As such, the compute device 200 can be configured to receive data (e.g., data files containing record sets, software updates and/or diagnostic tools, etc) from and/or send data to the other compute devices (e.g., the compute devices 152, 154 in FIG. 1) and/or other devices through one or more ports and/or antennas associated with the communications interface 230. In some embodiments, communications interface 230 can allow remote access to processor 250 by, for example, compute device 152, 154 in order to allow for software updates and/or diagnostic activities. Particularly, in some embodiments, one or more firewalls (e.g., the firewall 132 or 134 in FIG. 1) can be implemented at the communications interface 230, such that data transmitted through the communication interface 230 can be filtered appropriately.

The processor 250 can be any suitable processor configured to run and/or execute the module(s) included in the processor 250. Each module in the processor 250 can be any combination of hardware-based module (e.g., a field-programmable gate array (FPGA), an application specific integrated circuit (ASIC), a digital signal processor (DSP)) and/or software-based module (e.g., a module of computer code stored in memory and/or executed at the processor 250) capable of performing one or more specific functions associated with that module. Specifically, the match module 254 can be configured to perform a matching process for record sets, as described in detail with respect to FIG. 3 and FIGS. 4A-4L. Additionally, in some embodiments, the processor 250 can include other module(s) (not shown in FIG. 2) configured to perform other function(s) for the compute device 200. For example, the processor 250 can include a module configured to retrieve original record sets from other compute devices (e.g., the compute devices 152, 154 in FIG. 1) and transmit matched record sets to the other compute devices. For another example, the processor 250 can include a module configured to display record sets on a display device embedded within or coupled to the compute device 200.

In some embodiments, the memory 210 can be, for example, a random-access memory (RAM) (e.g., a dynamic RAM, a static RAM), a flash memory, a removable memory, and/or so forth. Data and information associated with performing the matching process for record sets can be stored, maintained and updated in the memory 210. Specifically, record sets (including original record sets to be matched and matched record sets as a result of performing the matching process) can be stored and updated in the record database 212 within the memory 210. Additionally, although not shown in FIG. 2, other data or information associated with performing the matching process for record sets can be stored in other portions of the memory 210. For example, instructions associated with performing the matching process can be stored (e.g., as an instruction set) in a non-transitory process-readable medium within the memory 210.

Figure 3:
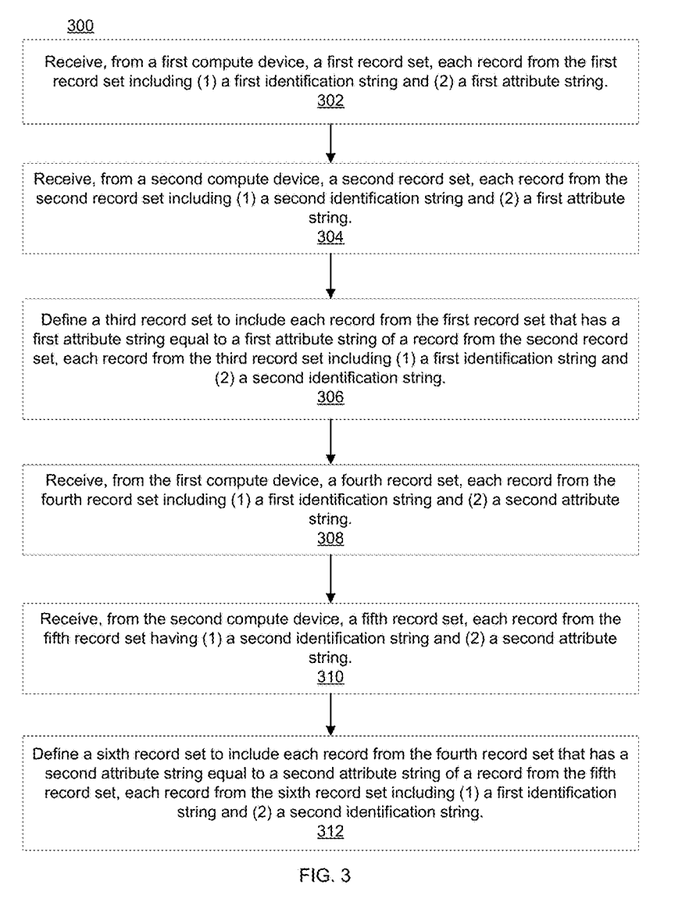
FIG. 3 is a flow chart illustrating a method for matching record sets, according to an embodiment.

FIG. 3 is a flow chart illustrating a method 300 for matching record sets, according to an embodiment. The method 300 can be performed at a compute device that is structurally and functionally similar to the compute device 110 and the compute device 200 shown and described with respect to FIGS. 1 and 2. Particularly, instructions associated with performing the method 300 can be stored in a memory of the compute device (e.g., the memory 210 of the compute device 200 in FIG. 2) and executed at a match module in a processor of the compute device (e.g., the match module 254 in the processor 250 of the compute device 200 in FIG. 2). An example of performing the method 300 is illustrated in detail with respect to FIGS. 4A-4L.

At 302, the match module can be configured to receive a first record set from a first compute device. For example, the first record set can be included in a data file sent from the first compute device to the compute device that hosts the match module. The first compute device can be structurally and functionally similar to the compute devices 152 and 154 shown and described with respect to FIG. 1. In some embodiments, the first record set can be defined and stored at the first compute device. In some other embodiments, the first record set can be defined at another device and then stored in the first compute device.

The first record set can be defined (e.g., at the first compute device) based on data associated with, for example, a first entity (e.g., a company, an organization, an individual) that owns or controls the first compute device. Furthermore, each record from the first record set can include at least a first identification string and a first attribute string associated with the first entity.

Each first identification string can be, for example, a text string (e.g., "user A"), a number (e.g., "999"), a code (e.g., "101a"), a symbol (e.g., "#"), combinations of the preceding, and/or in any other suitable format that can be included in the record. In some embodiments, each first identification string can be used to uniquely identify, for example, a user of the first entity. In other embodiments, more than one first identification string can be associated with, for example, a common user of the first entity.

Each first attribute string included in the first record set can be data representing a first attribute associated with, for example, a user of the first entity. The data can be, for example, a text string (e.g., "Lionel Messi"), a number (e.g., "21000"), or in any other format that is appropriate to represent the first attribute. The first attribute can be, for example, an email address of a user, a user's name or portion of a user's name (e.g., a surname, a first name), a delivery point (e.g., a delivery point associated with a delivery point barcode and/or an intelligent mail barcode, a complete address or portion of an address (e.g., a zip code, a city name), a combination of various items (e.g., a zip code and a surname), and/or the like. Thus, each pair of first identification string and first attribute string in a record from the first record set is associated with, for example, a user of the first entity.

At 304, the match module can be configured to receive a second record set from a second compute device different from the first compute device. For example, the second record set can be included in a data file sent from the second compute device to the compute device that hosts the match module. Similar to the first compute device, the second compute device can be structurally and functionally similar to the compute devices 152 and 154 shown and described with respect to FIG. 1. In some embodiments, the second record set can be defined and stored at the second compute device. In some other embodiments, the second record set can be defined at another device and then stored in the second compute device.

Similar to the first record set, the second record set can be defined (e.g., at the second compute device) based on data associated with, for example, a second entity (e.g., a company, an organization, an individual) that owns or controls the second compute device. The second entity can be different from the first entity. Furthermore, each record from the second record set can include at least a second identification string and a first attribute string associated with the second entity.

The second identification strings included in the second record set can be structurally similar to the first identification strings included in the first record set. In some embodiments, each second identification string can be used to uniquely identify, for example, a user of the second entity. In other embodiments, more than one second identification string can be associated with, for example, a common user of the second entity.

Similar to the first attribute strings included in the first record set, each first attribute string included in the second record set can be data representing the first attribute associated with, for example, a user of the second entity. The first attribute associated with the users of the second entity is the same as the first attribute associated with the users of the first entity. Such a first attribute can be, for example, an email address for a user of the first entity or a user of the second entity, a combination of zip code and surname of a user of the first entity or a user of the second entity, and/or the like. Each pair of second identification string and first attribute string in a record from the second record set is associated with, for example, a user of the second entity. Furthermore, a first attribute string in a record from the first record set can be identical to a first attribute string in a record from the second record set.

In some embodiments, the match module can be configured to receive the first record set from the first compute device, and receive the second record set from the second compute device, via one or more firewalls (e.g., the firewall 152, 154 in FIG. 1). In such embodiments, the first record set and the second record set received at the match module can be encrypted. For example, each first identification string in the first record set can be an encrypted value as a result of encrypting a raw first identification string using a first encryption key; and each second identification string in the second record set can be an encrypted value as a result of encrypting a raw second identification string using a second encryption key. The first encryption key can be different from the second encryption key. For another example, each first attribute string in the first record set can be a hashed value as a result of performing a hash function on raw data of a first attribute string associated with a user of the first entity; and each first attribute string in the second record data can be a hashed value as a result of performing the same hash function on raw data of a first attribute string associated with a user of the second entity. Particularly, as a result of applying the same hash function on the first attribute strings for the first record set and the second record set, a hashed first attribute string in the first record set and a hashed first attribute string in the second record set are identical if and only if their corresponding raw data of the first attribute string are identical. Examples of such first record set and second record set are illustrated with respect to FIGS. 4A-4L.

In some embodiments, more than one level of encryption can be implemented on the first record set and the second record set before they are received at the match module. In some embodiments, the encryption key(s) or the hash function is not available at the compute device that hosts the match module. As a result, the corresponding data in the first record set and the corresponding data in the second record set cannot be decrypted or recovered at the compute device. Thus, in such an embodiment, the raw data (e.g., a raw first identification string, a raw second identification string, raw data of a first attribute string) associated with the users of the first entity or the users of the second entity is not available at the compute device that hosts the match module.

In some embodiments, additional information associated with a record set (e.g., the first record set, the second record set) can be sent from a compute device (e.g., the first compute device, the second compute device) to the match module along with that record set. Such additional information can include, for example, a priority level for the attribute associated with the record set (e.g., the first attribute). For example, "email address" as an attribute has a priority level of 1 (i.e., the highest priority level); "combination of zip code and surname" as an attribute has a priority level of 2 (i.e., the second highest priority level); and "zip code" as an attribute has a priority level of 3 (i.e., the third highest priority level (or the lowest priority level)). Particularly, in the example of method 300, the priority level for the first record set is the same as the priority level for the second record set, since the attribute associated with the first record set (i.e., the first attribute) is the same as that associated with the second record set.

In some embodiments, the additional information such as the priority level can be sent to the match module separately from the record set. In other embodiments, such additional information can be included in the record set (e.g., as a third item in each record along with the other two items: an identification string and an attribute string) and thus sent to the match module as the record set being sent to the match module.

At 306, the match module can be configured to define a third record set based on the received first record set and second record set, such that the third record set includes each record from the first record set that has a first attribute string equal to a first attribute string of a record from the second record set. For each such record from the first record set, the third record set includes a record including the first identification string from that record from the first record set, as well as the second identification string from the corresponding record from the second record set (i.e., the record from the second record set that has the first attribute string equal to the first attribute string of that record from the first record set).

The match module can be configured to compare the first record set and the second record set to define the third record set in various methods. In some embodiments, for example, the match module can be configured to compare the first attribute string in each record from the first record set to the first attribute string in each record from the second record set. If the two first attribute strings are equal, the match module can be configured to retrieve the first identification string from the record from the first record set and retrieve the second identification string from the record from the second record set, and then define a new record in the third record set to include the retrieved first identification string and the retrieved second identification string. Thus, the third record set is defined after such a method is performed on each pair of a record from the first record set and a record from the second record set. In other embodiments, the third record set can be defined in any other suitable method.

In some embodiments, as described above, all the data (e.g., identification strings, attribute strings) included in the records from the first record set and the second record set is encrypted data (e.g., encrypted by an encryption key, hashed by a hash function). In such embodiments, the operations (e.g., comparison, matching) executed at the match module are performed on the encrypted data. As a result, the data (e.g., identification strings) included in the records from the third record set is also encrypted data.

At 308, similar to the step of 302, the match module can be configured to receive a fourth record set from the first compute device. The fourth record set can be defined based on data associated with the first entity. Each record from the fourth record set can include at least a first identification string and a second attribute string associated with the first entity. The number of records included in the fourth record set can be different from the number of records included in the first record set. A portion of the first identification strings included in the fourth record set can be identical to a portion of the first identification strings included in the first record set; while the second attribute strings included in the fourth record set are different from the first attribute strings included in the first record set, as the second attribute is different from the first attribute. Additionally, the second attribute has a priority level different than that of the first attribute. For example, the first attribute can be "email address," which has a priority level of 1; while the second attribute can be "combination of a zip code and a surname," which has a priority level of 2.

At 310, similar to the step of 304, the match module can be configured to receive a fifth record set from the second compute device. The fifth record set can be defined based on data associated with the second entity. Each record from the fifth record set can include at least a second identification string and a second attribute string associated with the second entity. The number of records included in the fifth record set can be different from the number of records included in the second record set. A portion of the second identification strings included in the fifth record set can be identical to a portion of the second identification strings included in the second record set; while the second attribute strings included in the fifth record set are different from the first attribute strings included in the second record set. Additionally, in some embodiments, data included in the fourth record set and the fifth record set can be encrypted similarly to data included in the first record set and the second record set.

At 312, similar to the step of 306, the match module can be configured to define a sixth record set based on the received fourth record set and fifth record set, such that the sixth record set includes each record from the fourth record set that has a second attribute string equal to a second attribute string of a record from the fifth record set. For each such record from the fourth record set, the sixth record set includes a record including the first identification string from that record from the fourth record set, as well as the second identification string from the corresponding record from the fifth record set (i.e., the record from the fifth record set that has the second attribute string equal to the second attribute string of that record from the fourth record set). Furthermore, similar to the third record set, the data (e.g., identification strings) included in the records from the sixth record set can be encrypted data.

In some embodiments, the method of defining a record set (e.g., the third record set, the sixth record set) based on two original record sets (e.g., the first and second record sets, the fourth and fifth record sets) can be repeated multiple times for multiple pairs of original record sets. In such embodiments, the original record sets can be paired based on different attributes of the users of the entities, which can be associated with different priority levels. For example, a first combined record set can be defined based on a first pair of original record sets for a first attribute "email address" with a priority level of 1; a second combined record set can be defined based on a second pair of original record sets for a second attribute "combination of zip code and surname" with a priority level of 2; a third combined record set can be defined based on a third pair of original record sets for a third attribute "zip code" with a priority level of 3; so on and so forth.

In some embodiments, the match module can be configured to perform a matching process based on two record sets (i.e., a record set that includes both first identification strings and second identification strings, and is defined based on two original record sets) such as the third record set and the sixth record set. Specifically, for example, the match module can be configured to define a matched record set based on the third record set and the sixth record set, such that 1) each record from the matched record set is a record from the third record set or a record from the sixth record set, and 2) the matched record set includes all or portion of the records from the third record set and the sixth record set. Such a matched record set can be defined based on the priority levels of the attributes associated with the third record set and the sixth record set, such that a record including a first identification string (and a second identification string) and associated with a lower priority level is excluded from the matched record set if another record including the same first identification string (and a second identification string) and associated with a higher priority level is included in the matched record set. Furthermore, each record from the third record set and the sixth record set is included in the matched record set if that record is not excluded by the above criterion.

For example, if the first attribute (e.g., "email address") is associated with a higher priority level and the second attribute (e.g., "zip code") is associated with a lower priority level, then each record from the third record set (including the first attribute strings) is included in the matched record set. For each record from the sixth record set (including the second attribute strings), if that record has a first identification string that is included in a record from the third record set, then that record from the sixth record set is excluded from the matched record set; otherwise that record from the sixth record set is included in the matched record set.

Additionally, note that the first identification and the second identification are exchangeable in such a matching process. That is, the order of receiving the first pair of record sets (i.e., the first record set and the second record set) and receiving the second pair of record sets (.e., the fourth record set and the fifth record set), which is equivalent to the order of the first identification and the second identification, can be exchangeable. In other words, the matching process can also be performed in a manner such that a record including a second identification string (and a first identification string) and associated with a lower priority level is excluded from the matched record set if and only if another record including the same second identification string (and a first identification string) and associated with a higher priority level is included in the matched record set.

In some embodiments, such a matching process described above can be implemented at the match module to define a matched record set based on more than two combined record sets that are associated with various priority levels for the attributes. As a result, each record including a first identification string and associated with a relatively lower priority level (from multiple priority levels) is excluded from the matched record set if and only if another record including the same first identification string and associated with a relatively higher priority level (from the multiple priority levels) is included in the matched record set.

The match module can be configured to implement the matching process described above in various methods. In some embodiments, the match module can be configured to implement a "dedupe-then-combine" method. For example, to match and combine the third record set with a higher priority level of attribute (i.e., the first attribute) and the sixth record set with a lower priority level of attribute (i.e., the second attribute), the match module can be configured to modify the sixth record set to a modified state to exclude each record from the sixth record set that has a first identification string equal to a first identification string of a record from the third record set. The match module can then be configured to combine the third record set and the sixth record set in the modified state to define a matched record set.

For another example, to match and combine the third record set with a priority level of 1 (i.e., the highest priority level), the sixth record set with a priority level of 2 (i.e., the second highest priority level) and a seventh record set (i.e., a combined record set) with a priority level of 3 (i.e., the third highest priority level), the match module can be configured to: 1) modify the sixth record set to a modified state to exclude each record from the sixth record set that has a first identification string equal to a first identification string of a record from the third record set; 2) modify the seventh record set to a modified state to exclude each record from the seventh record set that has a first identification string equal to a first identification string of a record from the third record set and each record from the seventh record set that has a first identification string equal to a first identification string of a record from the sixth record set; and 3) combine the third record set, the sixth record set in the modified state, and the seventh record set in the modified state to define a matched record set.

In some other embodiments, the match module can be configured to implement a "combine-then-dedupe" method. For example, to match and combine the third record set with a higher priority level of attribute (i.e., the first attribute) and the sixth record set with a lower priority level of attribute (i.e., the second attribute), the match module can be configured to combine the third record set and the sixth record set to define a matched record set in an initial state. The match module can then be configured to modify the matched record set in the initial state to a final state to exclude each record from the matched record set in the initial state that 1) has a first identification string equal to a first identification string of a record from the third record set, and 2) is associated with the sixth record set (or equivalently, associated with the second attribute).

For another example, to match and combine the third record set with a priority level of 1 (i.e., the highest priority level), the sixth record set with a priority level of 2 (i.e., the second highest priority level) and a seventh record set (i.e., a combined record set) with a priority level of 3 (i.e., the third highest priority level), the match module can be configured to 1) combine the third record set, the sixth record set and the seventh record set to define a matched record set in a first state; 2) modify the matched record set in the first state to a second state to exclude each record from the matched record set in the first state that (i) has a first identification string equal to a first identification string of a record from the third record set, and (ii) is associated with the sixth record set (or equivalently, associated with the second highest priority level) or associated with the seventh record set (or equivalently, associated with the third highest priority level); and 3) modify the matched record set in the second state to a third state (i.e., final state) to exclude each record from the matched record set in the second state that (i) has a first identification string equal to a first identification string of a record from the sixth record set, and (ii) is associated with the seventh record set (or equivalently, associated with the third highest priority level).

The two methods described above are examples of how to implement the matching process for two or more combined record sets. In some embodiments, the two methods can be combined in implementation. In other embodiments, the matching process can be implemented in any other suitable method. In some embodiments, the matched module can be configured to send a signal indicative of a matched record set to one or more compute devices that provide an original record set to the match module (e.g., the first compute device that provides the first record set and the fourth record set, the second compute device that provides the second record set and the fifth record set). Such a signal can be sent via, for example, a communications interface of the compute device that hosts the match module (e.g., the communications interface 230 of the compute device 200 in FIG. 2). Additionally, in some embodiments, the match module can be configured to send a combined record set such as the third record set or the sixth record set to the first compute device and/or the second compute device in a similar method.

In some embodiments, the priority levels associated with the attributes can be changed such that multiple combined record sets with various priority levels can be matched to define different matched record sets using the same method. As such, multiple matched record sets can be defined at the match module based on different order or priority levels associated with the attributes. The multiple matched record sets can further be compared and the best matched record set can be determined at the match module. In some embodiments, the match module can be configured to send the best matched record to one or more compute devices that provide an original record set to the match module (e.g., the compute devices 152, 154 in FIG. 1).

In some embodiments, a match module can define a report including characteristics of a matching process. In such an embodiment, the report can include, for example, a match rate (e.g., number of matches as a percent of total records) for each priority level, a number of matches for each priority level, a number of new matches (e.g. matches that are not excluded as duplicates) for a particular priority level, a cumulative number of matches as each priority level is added, and/or a cumulative match rate as each priority level is added. In such an embodiment, the match module can be configured to send a signal indicative of the report to one or more compute devices. In such an embodiment a compute device that receives the report can be configured to, for example, initiate an alarm and/or other notification if a match rate for each priority level is lower than a predetermined threshold for that priority level (or associated attribute) or for a particular combination of priority levels (or associated attributes), that a total number of matches is below a predetermined threshold for that priority level (or associated attribute) or for a particular combination of priority levels (or associated attributes), etc. In some embodiments, such a report can be used to manually and or automatically select which priority levels to use in a final matched record set and/or which order to deduplicate a matched record set as described herein.

FIGS. 4A-4L illustrate a process of matching record sets, according to an embodiment. The process illustrated in FIGS. 4A-4L is an example with reference to the method 300 shown and described with respect to FIG. 3. The process can be executed at a match module similar to the match module 254 in FIG. 2 and the match module described with respect to FIG.

3, in coordination with compute devices shown and described with respect to FIGS. 1-3 (e.g., the compute devices 152, 154, 110 in FIG. 1, the compute device 200 in FIG. 2).

Figure 4A:
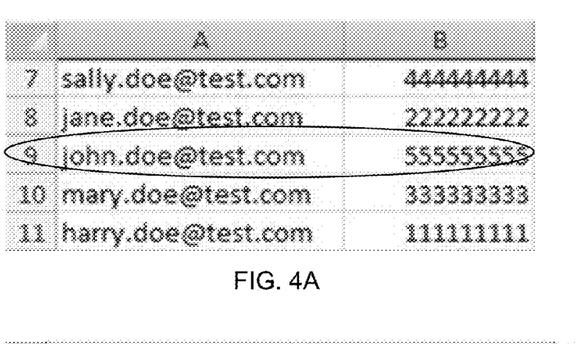
FIGS. 4A-4L illustrate a process of matching record sets, according to an embodiment.

FIGS. 4A-4D illustrate a first set of record sets that are defined at the compute devices and/or sent from the compute devices to the match module. Specifically, FIG. 4A shows a first record set including raw data (i.e., not encrypted or hashed) that is defined at a first compute device (e.g., the compute device 152 in FIG. 1). The first record set includes data associated with a first attribute, email address, for users of a first entity (e.g., registered users of a website). As shown in FIG. 4A, the first record set includes at least an index column and two content columns: index column at the leftmost position, which includes an index (e.g., 7, 8) for each record stored in the first record set; column A of first attribute strings (e.g., sally.doe@test.com, jane.doe@test.com), which are email addresses of the users of the first entity; and column B of first identification strings (e.g., 444444444, 222222222), which are identifications associated with the corresponding users of the first entity. Thus, each record in the first record set includes a first attribute string (e.g., mary.doe@test.com) and a first identification string (e.g., 333333333) associated with a user of the first entity.

Figure 4B:
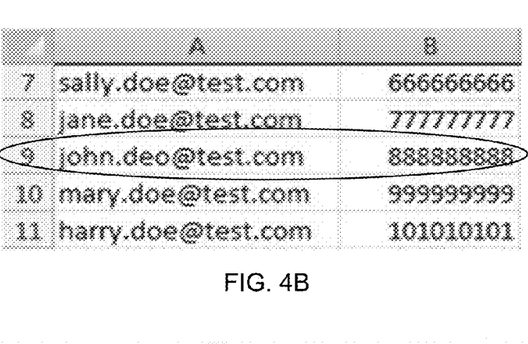
Figure 4C:
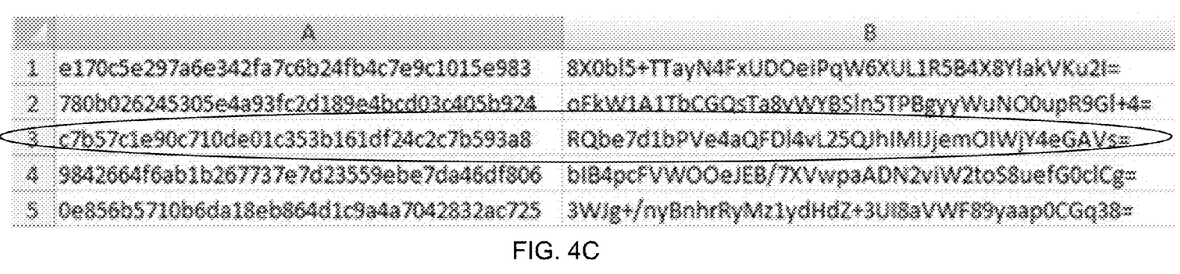

FIG. 4C shows a first encrypted record set that is encrypted from the first record set in FIG. 4A. Specifically, each first identification string (e.g., 555555555) in a record of the first record set is encrypted to produce, by using a first encryption key at the first compute device, an encrypted first identification string (e.g., "RQbe7d1bPVe4aQFDI4vL25QJhIMIJjemOlWjY4eGAVs=") that is stored in column B of a corresponding record of the first encrypted record set. Each first attribute string (e.g., john.doe@test.com) in a record of the first record set is hashed to produce, by using a hash function at the first compute device, a hashed first attribute string (e.g., "c7b57c1e90c710de01c353b161df24c2c7b593a8") that is stored in column A of a corresponding record of the first encrypted record set.

Similar to FIG. 4A, FIG. 4B shows a second record set including raw data (i.e., not encrypted) that is defined at a second compute device (e.g., the compute device 154 in FIG. 1). The second record set includes data associated with the first attribute for users of a second entity (e.g., shoppers at a retail chain store). As shown in FIG. 4B, the second record set includes an index column and two content columns: index column at the leftmost position, which includes an index (e.g., 7, 8) for each record stored in the second record set; column A of first attribute strings (e.g., sally.doe@test.com, jane.doe@test.com), which are email addresses of the users of the second entity; and column B of second identification strings (e.g., 666666666, 777777777), which are identifications associated with the corresponding users of the second entity. Thus, each record in the second record set includes a first attribute string (e.g., mary.doe@test.com) and a second identification string (e.g., 999999999) associated with a user of the second entity.

Figure 4D:
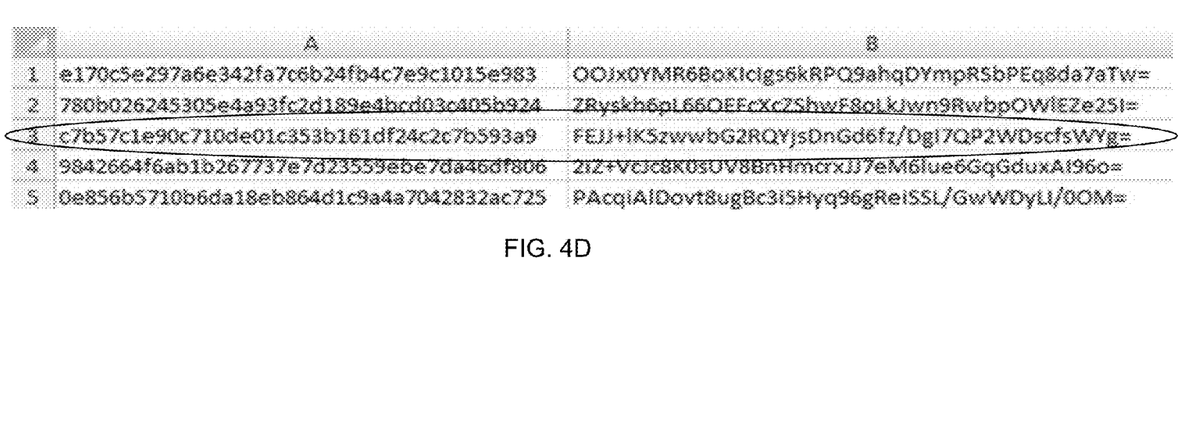

Similar to FIG. 4C, FIG. 4D shows a second encrypted record set that is encrypted from the second record set in FIG. 4B. Specifically, each second identification string (e.g., 777777777) in a record of the second record set is encrypted to produce, by using a second encryption key (can be different from the first encryption key used at the first compute device) at the second compute device, an encrypted second identification string (e.g., "FEJJ+1K5zwwbG2RQYjsDnGd6fz/Dg17QP2WDscfsWYg=") that is stored in column B of a corresponding record of the second encrypted record set. Each first attribute string (e.g., john.deo@test.com) in a record of the second record set is hashed to produce, by using the hash function (same as that used at the first compute device) at the second compute device, a hashed first attribute string (e.g., "c7b57c1e90c710de01c353b161df24c2c7b593a9") that is stored in column A of a corresponding record of the second encrypted record set.

Figure 4E:
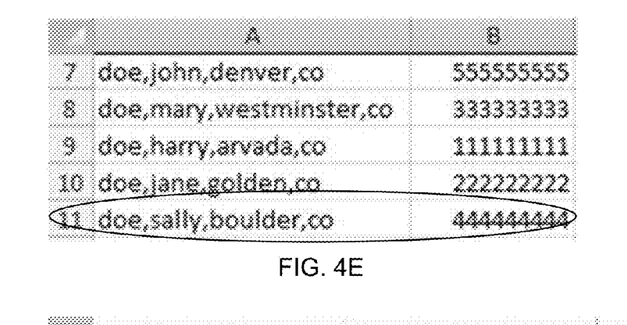

Similar to FIGS. 4A-4D, FIGS. 4E-4H illustrate a second set of record sets that are defined at the compute devices and/or sent from the compute devices to the match module. Specifically, similar to FIG. 4A, FIG. 4E shows a third record set including raw data that is defined at the first compute device. The third record set includes data associated with a second attribute, name and address (specifically, a combination of last name, first name, city and state), for users of the first entity. As shown in FIG. 4E, the third record set includes at least an index column and two content columns: index column at the leftmost position, which includes an index for each record stored in the third record set; column A of second attribute strings, which are names and addresses of the users of the first entity; and column B of first identification strings, which are identifications associated with the corresponding users of the first entity. Thus, each record in the third record set includes a second attribute string and a first identification string associated with a user of the first entity.

Figure 4F:
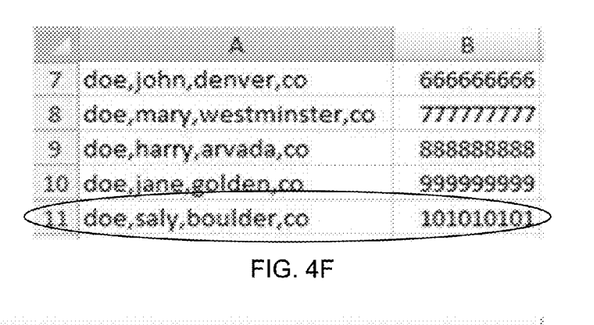
Figures 4G, 4H:
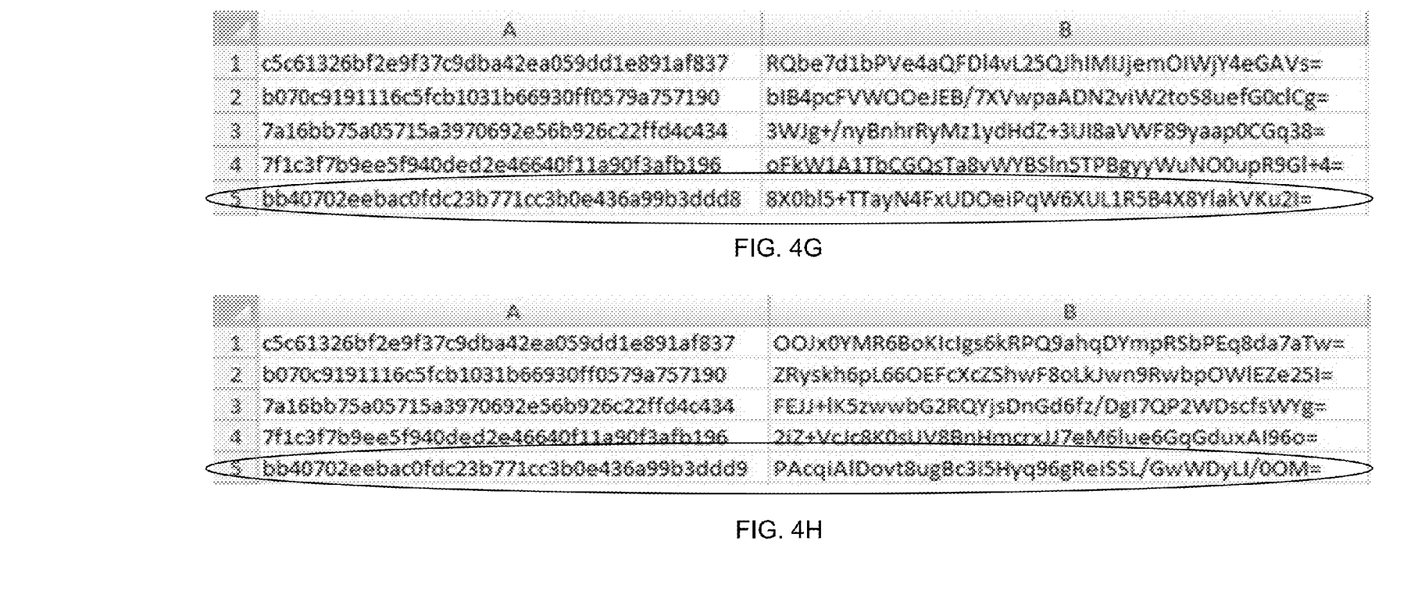

Similar to FIG. 4C, FIG. 4G shows a third encrypted record set that is encrypted from the third record set in FIG. 4E. Specifically, each first identification string in a record of the third record set is encrypted to produce, by using the first encryption key at the first compute device, an encrypted first identification string that is stored in column B of a corresponding record of the third encrypted record set. Each second attribute string in a record of the third record set is hashed to produce, by using the hash function at the first compute device, a hashed second attribute string that is stored in column A of a corresponding record of the third encrypted record set.

Similar to FIG. 4B and FIG. 4E, FIG. 4F shows a fourth record set including raw data that is defined at the second compute device. The fourth record set includes data associated with the second attribute for users of the second entity. As shown in FIG. 4F, the fourth record set includes at least an index column and two content columns: index column at the leftmost position, which includes an index for each record stored in the fourth record set; column A of second attribute strings, which are names and addresses of the users of the second entity; and column B of second identification strings, which are identifications associated with the corresponding users of the second entity. Thus, each record in the fourth record set includes a second attribute string and a second identification string associated with a user of the second entity.

Similar to FIG. 4G and FIG. 4D, FIG. 4H shows a fourth encrypted record set that is encrypted from the fourth record set in FIG. 4F. Specifically, each second identification string in a record of the fourth record set is encrypted to produce, by using the second encryption key at the second compute device, an encrypted second identification string that is stored in column B of a corresponding record of the fourth encrypted record set. Each second attribute string in a record of the fourth record set is hashed to produce, by using the hash function at the second compute device, a hashed second attribute string that is stored in column A of a corresponding record of the fourth encrypted record set.

Figure 4I:
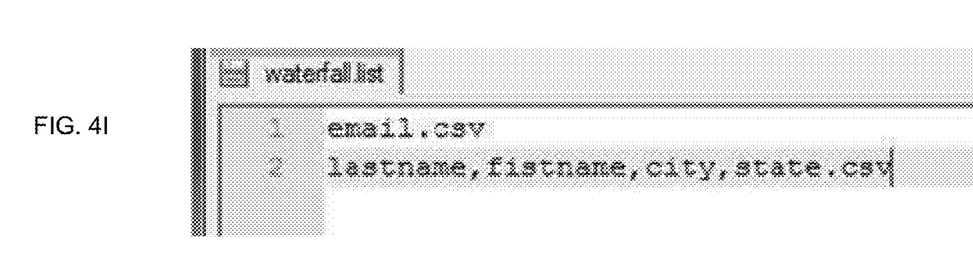

FIG. 4I illustrates a screen shot of a configuration file (waterfall.list as shown in FIG. 4I) that stores information of the first attribute (i.e., email) and the second attribute (i.e., a combination of last name, first name, city and state). In some embodiments, information associated with the priority levels for the first attribute and the second attribute can also be stored in such a configuration file. In the example of FIG. 4I, the first attribute is associated with an index 1 and the second attribute is associated with an index 2, which, in some embodiments, indicates that the priority level for the first attribute is higher than that for the second attribute. In some embodiments, such a configuration file can be stored in, for example, a memory associated with the match module (e.g., the memory 210 that is associated with the match module 254 in FIG. 2), and retrieved by the match module to facilitate performing the matching method when needed.

Figure 4J:
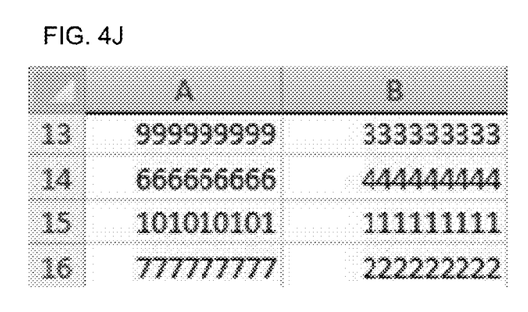
Figure 4K:
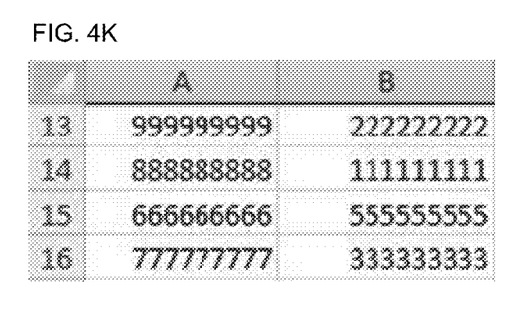
Figure 4L:
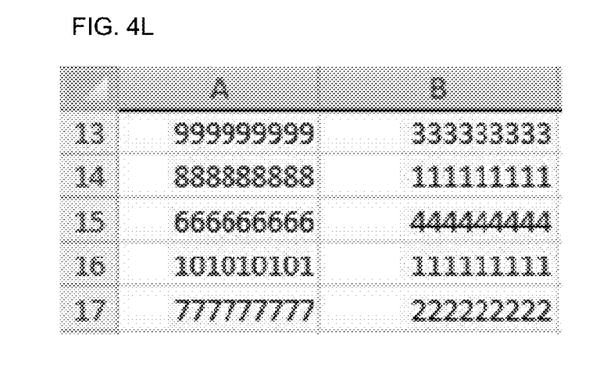

FIGS. 4J-4L illustrate results (intermediate combined record sets in FIGS. 4J and 4K and a final matched record set in FIG. 4L) of performing the matching process described in FIG. 3 on the record sets shown in FIGS. 4A-4H. Note that the record sets shown in FIGS. 4J-4L are decrypted versions for illustration and explanation purpose. Such a decrypted record set is typically not available at the match module or any other compute device (e.g., the first compute device, the second compute device), since the first encryption key and the second encryption key are typically not available at any single compute device at the same time.

The first compute device can send the first encrypted record set (shown in FIG. 4C) and the third encrypted record set (shown in FIG. 4G) to the match module; and the second compute device can send the second encrypted record set (shown in FIG. 4D) and the fourth encrypted record set (shown in FIG. 4H) to the match module. The match module can be configured to compare and combine the first encrypted record set and the second encrypted record set to define a first combined encrypted record set (not shown in the figures) according to the method described in step 306 and 312 in FIG. 3. FIG. 4J shows a decrypted version of the first combined encrypted record set. As shown in FIGS. 4A and 4B, since the first attribute string in the record with index 9 in the first record set (the email address john.doe@test.com highlighted in the circle in FIG. 4A) is different from the first attribute string in the record with index 9 in the second record set (the email address john.deo@test.com highlighted in the circle in FIG. 4B), these two records do not match. Each other record in the first record set matches a record in the second record set (in terms of the first attribute strings), and vice versa. As a result, the encrypted first identification strings in the matched records from the first record set and the encrypted second identification strings in the matched records from the second record set are included in the first combined encrypted record set, whose decrypted version is shown in FIG. 4J.

Similarly, the match module can be configured to compare and combine the third encrypted record set and the fourth encrypted record set to define a second combined encrypted record set (not shown in the figures) according to the method described in step 306 and 312 in FIG. 3. FIG. 4K shows a decrypted version of the second combined encrypted record set. As shown in FIGS. 4E and 4F, since the second attribute string in the record with index 11 in the third record set ("doe, sally, boulder, co" as highlighted in the circle in FIG. 4E) is different from the second attribute string in the record with index 11 in the fourth record set ("doe, saly, boulder, co" as highlighted in the circle in FIG. 4F), these two records do not match. Each other record in the third record set matches a record in the fourth record set (in terms of the second attribute strings), and vice versa. As a result, the encrypted first identification strings in the matched records from the third record set and the encrypted second identification strings in the matched records from the fourth record set are included in the second combined encrypted record set, whose decrypted version is shown in FIG. 4K.

Furthermore, the match module can be configured to, according to the matching method described with respect to FIG. 3, match and integrate the first combined encrypted record set (whose decrypted version is shown in FIG. 4J) and the second combined encrypted record set (whose decrypted version is shown in FIG. 4K) to define a final matched record set (whose decrypted version is shown in FIG. 4L). Particularly, because the first attribute (i.e., email address) has a higher priority than the second attribute (i.e., name and address) according to the configuration file in FIG. 4I, the records from the first combined encrypted record set (which is associated with the first attribute) have a higher priority than the records from the second combined encrypted record set (which is associated with the second attribute). As a result, each record from the first combined encrypted record set is included in the final matched record set; while each record from the second combined encrypted record set is included in the final matched record set if and only if that record does not have an encrypted first identification string equal to an encrypted first identification string in a record from the first combined encrypted record set. As shown in the decrypted versions in FIGS. 4J-4L, each record from the decrypted record set of FIG. 4J is included in the decrypted record set of FIG. 4L; while only the record with index 14 from the decrypted record set of FIG. 4K is included in the decrypted record set of FIG. 4L, as the other three records (with indexes 13, 15 and 16) from the decrypted record set of FIG. 4K have a first identification string (i.e., 999999999, 666666666, 777777777) equal to a first identification string in a record from the decrypted record set of FIG. 4J.

While shown and described above with respect to FIGS. 3-4L as a combined record set (e.g., the third record set or the sixth record set described in the method 300 in FIG. 3) being defined based on two original record sets (e.g., the first and second record sets described in the method 300, the fourth and fifth record sets described in the method 300), in other embodiments, such a combined record set can be defined based on more than two original record sets in a similar method. In such embodiments, the combined record set can include more than two identification strings. For example, a combined record set can be defined based on three original record sets by defining each record of the combined record set to include a first identification string in a record from the first original record set, a second identification string in a record from the second original record set, and a third identification string in a record from the third original record set, where each of the three records includes a common attribute string.

While the record sets shown and described with respect to FIGS. 4A-4L include index columns, in some embodiments, a record set can exclude index columns. In such embodiments, a priority level of a record in a matched record set can be indicated based on the order of the records in the record set unrelated to any column and/or row index. In some embodiments, a record and/or record entry can include metadata indicative of a priority level and/or associated attribute. In such embodiments, whether to include a record in a combined record set (e.g., whether or not to delete a duplicate entry, and which entry to delete) can be based on the order of the record and/or record entry and/or associated meta data.

While the record sets are described herein as including records associated with customers and/or users, in some embodiments, record sets can include manufactured and/or otherwise known records such that a match module can check the accuracy of a match. For example, a first entity can include a known record in a record set sent to the match module. Similarly, a second entity can include the same known record in a record set sent to the match module. In this manner, after the match module compares the record set from the first entity to the record set from the second entity, the match module can confirm that the known record is included in the matched record set. In such embodiments, the presence of the known record in the matched record set can confirm that the matching method is working, that a hash function used on records in the record sets was implemented properly, and/or that encryption used on the data file including a record set was implemented properly. In some embodiments, each pair of record sets (i.e. each pair of record sets associated with a priority level) can include a different known record.

The record sets, matched record sets, data files, etc, are described herein in various embodiments as including raw data, encrypted data and/or hashed data. In some embodiments, data can be transferred between entities without any encryption and/or hashing, encrypted and/or hashed data files with raw (not encrypted and/or hashed) data, and/or unencrypted data files with encrypted and/or hashed data. For example, a data file can be transmitted (encrypted or unencrypted) from one entity to another entity; and the data file can include a record set with a list of hashed, encrypted and/or raw identification strings each associated with a hashed, encrypted and/or raw attribute string. In some embodiments, a first entity, for example a data analytics entity, can match data with more than one other entity. In such embodiments, the data analytics entity can have access to a unique hash salt for each of the other entity, and each of the other entities can have only their unique hash salt.

In some embodiments described herein, a record set can be prepared at a first compute device and sent to a second compute device. For example, a first compute device can prepare a first record set that includes a first list of first identification strings associated with first attribute strings, and prepare a second record set that includes at least a portion of the list of first identification strings associated with second attribute strings. The first compute device can hash and/or encrypt (or leave raw) the first identification strings, the first attribute strings and/or the second attribute strings, and can encrypt (or leave unencrypted) the first record set and/or the second record set, and can send the record set to another compute device, including the compute device having a match module. In other embodiments, the first compute device can send one or more unprepared data files including one or more record sets that include the first identification strings, the associated first attribute strings and the associated second attribute strings. In such an embodiment, the compute device that receives the one or more unprepared data files can combine the data files, if necessary, and can prepare the first record set, to include the first identification strings and associated first attribute strings, and can prepare the second record set, to include the first identification strings and associated first attribute strings, and can send the first record set and/or the second record set to the match module. In some embodiments, the compute device having the match module can receive prepared records sets (e.g., record sets that a prepared to be matched) as well as unprepared record sets (e.g., record sets that are not prepared to be matched). In some embodiments, preparing a record set can include adding a hash salt to each record in a record set, e.g. adding the hash salt to each attribute string in a record set. In such an embodiment, records, specifically attribute strings, in a pair of record sets to be matched can include the same hash salt such that records having the same first attribute string will match.

While the match modules described above match records based on a record from one record set having an equal attribute string with a record from another record set, in other embodiments, a match module can match records based on from one record set having a probabilistically equivalent attribute string with a record from another record set. For an example, an attribute string associated with johndoe434@firstprovider.com can be probabilistically equivalent with an attribute string associated with johndoe434@secondprovider.com. Said another way, it is probable (e.g. above a predetermined degree of certainty) that a user associated with johndoe434@firstprovider.com is the same user as johndoe434@secondprovider.com, even though the attribute strings are not identical. Other examples can include matching nicknames with full names, etc.

While the methods described above related to having two or three attributes and associated priority levels. In other embodiments, more or fewer attributes and associates priority levels can be used. For an example, a method can include five attributes each associated with a priority level. In such an example, a match module can receive and compare five pairs of original record sets to define five combined record sets. Continuing with this example, the match module can define a plurality of matched record sets using any combination of the five combined record sets and can compare each matched record set from that plurality of matched record sets and choose one matched record set based on predetermined criteria. In such an example, the predetermined criteria can include, for example, maximum or minimum number of records in the matched record set (e.g., at least 1,000 matched records), maximum or minimum amount of priority levels included in the matched record set (e.g., no more than 3 of 5 priority levels), required priority levels, etc, and combinations of these. For example, predetermined criteria could include that the matched set must include the combined record sets associated with priority levels 1 and 2, no more than 4 of 5 combined record sets, and the matched record set with the maximum number of records that meets the first two criteria.

It is intended that the systems and methods described herein can be performed by software (stored in memory and/or executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including Unix utilities, C, C++, Java™, Ruby, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices (e.g., wireless access points, mobile communication devices) with a non-transitory computer-readable medium (also can be referred to as a non-transitory processor-readable medium or memory) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

While various embodiments have been described above, it should be understood that they have been presented by way of example only, and not limitation. Where methods and steps described above indicate certain events occurring in certain order, the ordering of certain steps may be modified. Additionally, certain of the steps may be performed concurrently in a parallel process when possible, as well as performed sequentially as described above. Although various embodiments have been described as having particular features and/or combinations of components, other embodiments are possible having any combination or sub-combination of any features and/or components from any of the embodiments described herein. Furthermore, although various embodiments are described as having a particular entity associated with a particular compute device, in other embodiments different entities can be associated with other and/or different compute devices. For example, while compute device 152 and computer device 110 are described as being associated with an online entity, and compute device 154 is described as being associated with a data analytics entity, in other embodiments, compute device 152 and computer device 110 can be associated with a data analytics entity and compute device 110 can be associated with an online entity.

What is claimed is:

1. A method, comprising:
   receiving, from a first compute device, a first record set, each record from the first record set including (1) an encrypted first identification string and (2) a hashed first attribute string;
   receiving, from a second compute device, a second record set, each record from the second record set having (1) an encrypted second identification string and (2) a hashed first attribute string;
   defining a third record set to include each record from the first record set that has a hashed first attribute string equal to a hashed first attribute string of a record from the second record set, each record from the third record set including (1) an encrypted first identification string and (2) an encrypted second identification string;
   receiving, from the first compute device, a fourth record set, each record from the fourth record set including (1) an encrypted first identification string and (2) a hashed second attribute string;
   receiving, from the second compute device, a fifth record set, each record from the fifth record set having (1) an encrypted second identification string and (2) a hashed second attribute string;
   defining a sixth record set to include each record from the fourth record set that has a hashed second attribute string equal to a hashed second attribute string of a record from the fifth record set, each record from the sixth record set including (1) an encrypted first identification string and (2) an encrypted second identification string;
   modifying the sixth record set to a modified state to exclude each record from the sixth record set that has an encrypted first identification string equal to an encrypted first identification string of a record from the third record set;
   defining a matched record set to include (1) each record from the third record set and (2) each record from the sixth record set in the modified state; and
   sending, to the second compute device, a signal indicative of the matched record set.

2. The method of claim 1, wherein each hashed first attribute string from the first record set is based on an email address.

3. The method of 1, further comprising
   receiving, from the first compute device, a seventh record set, each record from the seventh record set including an encrypted first identification string and a hashed third attribute string;
   receiving, from the second compute device, an eighth record set, each record from the eighth record set having an encrypted second identification string and a hashed third attribute string; and
   defining a ninth record set to include each record from the seventh record set that has a hashed third attribute string equal to a hashed third attribute string of a record from the eighth record set, each record from the ninth record set including (1) an encrypted first identification string and (2) and an encrypted second identification string.

4. The method of 3, further comprising:
   modifying the ninth record set to a modified state to exclude (1) each record from the ninth record set that has an encrypted first identification string equal to an encrypted first identification string of a record from the third record set and (2) each record from the ninth record set that has an encrypted first identification string equal to an encrypted first identification string of a record from the sixth record set;
   modifying the matched record set to a modified state to include (1) each record from the third record set, (2) each record from the sixth record set in the modified state, and (3) each record from the ninth record set in the modified state; and
   sending, to the first compute device, a signal indicative of the matched record set in the modified state.

5. The method of claim 1, wherein each hashed second attribute string from the fourth record set is based on a zip code and on a portion of a name.

6. An apparatus, comprising:
   a match module implemented in at least one of a memory or a processing device, the match module configured to receive, from a first compute device, a first record set, each record from the first record set including (1) an encrypted first identification string and (2) a hashed first attribute string;
   the match module configured to receive, from a second compute device different from the first compute device, a second record set, each record from the second record set having (1) an encrypted second identification string and (2) a hashed first attribute string;
   the match module configured to define a matched record set to include each record from the first record set that has a hashed first attribute string equal to a hashed first attribute string of a record from the second record set, each record from the matched record set including (1) an encrypted first identification string and (2) an encrypted second identification string;

the match module configured to receive, from the first compute device, a third record set, each record from the third record set including (1) an encrypted first identification string and (2) a hashed second attribute string;

the match module configured to receive, from the second compute device, a fourth record set, each record from the fourth record set having (1) an encrypted second identification string and (2) a hashed second attribute string;

the match module configured to modify the matched record set to a first modified state to include each record from the third record set that has a hashed second attribute string equal to a hashed second attribute string of a record from the fourth record set, each record from the matched record set in the first modified state including (1) an encrypted first identification string and (2) an encrypted second identification string;

the match module configured to modify the matched record set to a second modified state to exclude each record from the matched record set in the first modified state that (1) has an encrypted first identification string equal to an encrypted first identification string of a record from the first record set and (2) is associated with the third record set and the fourth record set;

the match module configured to send, to the second compute device, a signal indicative of the matched record set in the second modified state.

7. The apparatus of claim 6, wherein the match module is configured to be operatively coupled to the first compute device via a firewall.

8. The apparatus of claim 6, wherein the match module is configured to be (1) disposed behind a first firewall, (2) operatively coupled to the second compute device disposed behind the first firewall, and (3) operatively coupled, via the first firewall, to the first compute device disposed behind a second firewall, different from the first firewall.

9. The method of claim 6, wherein each hashed first attribute string from the first record set is based on an email address.

10. The apparatus of claim 6, wherein a first attribute associated with each hashed first attribute string from the first record set has a higher historic match accuracy value than a second attribute associated with each hashed second attribute string from the third record set.

11. A non-transitory processor-readable medium storing code representing instructions to cause a processor to perform a process, the code comprising code to:

receive, from a first compute device, a first record set, each record from the first record set including (1) a first identification string and (2) a first attribute string;

receive, from a second compute device, a second record set, each record from the second record set having (1) a second identification string and (2) a first attribute string;

define a third record set to include each record from the first record set that has a first attribute string equivalent to a first attribute string of a record from the second record set, each record from the third record set including (1) a first identification string and (2) a second identification string;

receive, from the first compute device, a fourth record set, each record from the fourth record set including (1) a first identification string and (2) a second attribute string;

receive, from the second compute device, a fifth record set, each record from the fifth record set having (1) a second identification string and (2) a second attribute string;

define a sixth record set to include each record from the fourth record set that has a second attribute string equivalent to a second attribute string of a record from the fifth record set, each record from the sixth record set including (1) a first identification string and (2) a second identification string;

modify the sixth record set to a modified state to exclude each record from the sixth record set that has a first identification string equivalent to a first identification string of a record from the third record set;

define a matched record set to include (1) each record from the third record set and (2) each record from the sixth record set in the modified state; and send, to the second compute device, a signal indicative of the matched record set.

12. The non-transitory processor-readable medium storing code representing instructions to cause a processor to perform a process of claim 11, wherein:

each record from the first record set includes (1) a first identification string that was encrypted by the first compute device using an encryption function and (2) a first attribute string that was hashed by the first compute device using a hash function; and each record from the second record set includes (1) a first identification string that was encrypted by the second compute device using the encryption function and (2) a first attribute string that was hashed by the second compute device using the hash function.

13. The non-transitory processor-readable medium storing code representing instructions to cause a processor to perform a process of claim 11, the code further comprising code to:

receive, from the first compute device, a seventh record set, each record from the seventh record set including a first identification string and a third attribute string;

receive, from the second compute device, an eighth record set, each record from the eighth record set having a second identification string and a third attribute string; and define a ninth record set to include each record from the seventh record set that has a third attribute string equivalent to a third attribute string of a record from the eighth record set, each record from the ninth record set including (1) a first identification string and (2) a second identification string.

14. The non-transitory processor-readable medium storing code representing instructions to cause a processor to perform a process of claim 13, the code further comprising code to:

modify the ninth record set to a modified state to exclude (1) each record from the ninth record set that has a first identification string equal to a first identification string of a record from the third record set and (2) each record from the ninth record set that has a first identification string equal to a first identification string of a record from the sixth record set;

modify the matched record set to a modified state to include (1) each record from the third record set, (2) each record from the sixth record set in the modified state, and (3) each record from the ninth record set in the modified state; and send, to the first compute device, a signal indicative of the matched record set in the modified state.

15. The non-transitory processor-readable medium storing code representing instructions to cause a processor to perform a process of claim 11, wherein each first attribute string from the first record set is based on a surname and on a zip code.

16. The non-transitory processor-readable medium storing code representing instructions to cause a processor to perform a process of claim 11, wherein the first record set includes a first known record, the second record set includes the first known record, the fourth record set includes a second known record, the fifth record set includes the second known record the code further comprising code to confirm that the third record set includes the first known record and that the sixth record set includes the second known record.

* * * * *